United States Patent
Dragan et al.

[11] Patent Number: 5,489,207
[45] Date of Patent: Feb. 6, 1996

[54] DENTAL CARTRIDGE EXTRUDER WITH RIGID DROP-IN FRONT END

[75] Inventors: William B. Dragan, Easton; John J. Discko, Jr., Hamden, both of Conn.

[73] Assignee: Centrix, Inc., Shelton, Conn.

[21] Appl. No.: 147,719

[22] Filed: Nov. 4, 1993

[51] Int. Cl.⁶ ........................................ A61C 5/04
[52] U.S. Cl. ........................................ 433/90
[58] Field of Search ............... 433/89, 90; 604/232, 604/234, 235; 222/325, 326, 327, 386

[56] References Cited

U.S. PATENT DOCUMENTS

| | | |
|---|---|---|
| 3,076,455 | 2/1963 | McConnaughey et al. . |
| 3,220,412 | 11/1965 | McConnaughey et al. . |
| 4,198,756 | 4/1980 | Dragan ................... 222/326 |
| 4,295,828 | 10/1981 | Rudler ................... 433/90 |
| 4,330,280 | 5/1982 | Dougherty et al. ......... 433/90 |
| 4,384,853 | 5/1983 | Welsh ................... 433/90 |
| 4,391,590 | 7/1983 | Dougherty ................ 433/90 |
| 5,061,179 | 10/1991 | Dragan ................... 433/90 |
| 5,125,836 | 6/1992 | Dragan et al. ............ 433/90 |
| 5,306,147 | 4/1994 | Dragan et al. ............ 433/90 |

FOREIGN PATENT DOCUMENTS 5701465  7/1979  Brazil .

*Primary Examiner*—Nicholas D. Lucchesi
*Attorney, Agent, or Firm*—Fattibene and Fattibene; Paul A. Fattibene; Arthur T. Fattibene

[57] ABSTRACT

A manual dental extruder or syringe gun having a front end with rigid side walls and an opening therein adapted to receive a dental cartridge, capsule, ampule or tip having a flange. The body portion of the cartridge has a diameter less than that of the lateral width of the opening in the rigid side walls so that the dental cartridge can easily be dropped therein. At one end of the cartridge opening is a flange retainer. After dropping the dental cartridge in the front end, the cartridge is slid forward into the flange retainer. A portion of the rigid side walls extend over the flange when the dental cartridge is in position to be extruded. The rigid side walls improve the durability and strength of the dental extruder and prevents the dental cartridge from being pushed through the end of the extruder due to the large longitudinal forces required to extrude viscous dental materials.

18 Claims, 4 Drawing Sheets

DENTAL CARTRIDGE EXTRUDER WITH RIGID DROP-IN FRONT END

FIELD OF THE INVENTION

This invention relates generally to a dental device for the placement of dental materials, and more particularly to a dental syringe device having an improved barrel front end portion for the extrusion of dental cartridges containing dental materials.

BACKGROUND OF THE INVENTION

With the discovery of new dental filling materials, different techniques and apparatus for placing these new dental filling materials have been developed. The earliest known delivery system for use with composite resin type materials is disclosed in U.S. Pat. No. 3,581,399 issuing to Dragan on Jun. 1, 1971. Therein disclosed is a manual extruder for dispensing viscous dental material within a prepared tooth. A further improved delivery system is disclosed in U.S. Pat. No. 4,198,756 issuing to Dragan on Apr. 22, 1980. The device disclosed therein provides a mechanical advantage for the controlled dispensing of the more viscous dental materials. These devices permit improved dental filling techniques in that the viscous material is placed in the tooth cavity from the bottom up. This eliminates voids in the tooth filling and is an improvement over prior filling techniques. Since these initial disclosures of an extruding system for dispensing dental material contained in cartridges, there have been many improvements in devices to dispense the dental material as well as the containers or cartridges therefor. Most of these improvements have been directed to ease of use and efficient dispensing of the ever increasing viscous nature of newer dental materials.

Initially, a "snap-fit" front end was believed to be desirable in a dental extrusion device because of its inherent ease of use. A dental cartridge containing dental material could easily be snapped into the front end of a dental extruder. Examples of such "snap-fit" front end portions of a dental extruder are disclosed in U.S. Pat. Nos. 4,330,280 and 4,384,853. Therein disclosed is a dental extruder having flexible side walls that permit a cartridge to be snapped into the front end. The width of the front end opening is slightly less than the outside lateral width or diameter of a cartridge. Therefore, the insertion of the cartridge causes the side walls to flex, resulting in the "snap-fit". While the "snap-fit" front end dental extruders are relatively easy to use, the inherent flexibility necessary to provide a "snap-fit" results in a potentially hazardous condition. Some dental materials that are extremely viscous and placed into dental cartridges for extrusion with a dental extruder result in extremely high forces being applied to the front end. These high forces, when applied to a "snap-fit" front end often causes the flexible side walls to be forcibly spread apart during use. This results in the dental cartridge becoming wedged within the front end or even more seriously, the cartridge unintentionally shooting from the front end during use. This creates a potentially hazardous situation in that during the normal use, the front end of the dental extruder is inside a patient's mouth. Additionally, constant flexing of the side walls results in fatigue and often breakage. U.S. Pat. No. 5,061,179 entitled "Manual Extruder and Cartridge Having Interlocking Bearing Surfaces" issuing to Dragan on Oct. 29, 1991, discloses a dental extruder and cartridge attempting to overcome some of the problems encountered with the "snap-fit" front end. Therein disclosed is a dental extruder and cartridge having interlocking bearing surfaces. The interlocking bearing surfaces helped prevent the flexible side walls from spreading apart during extrusion of the more viscous dental materials. While this helped solve some of the problems inherent with a "snap-fit" front end, it did not solve the fatigue problem of repeated use and flexing of the side walls or the stress placed on the cartridge by the side walls.

Therefore, there is a need for an easy loading dental extruder with high strength and durability that can safely and confidently be used with dental materials having high viscosity.

SUMMARY OF THE INVENTION

The present invention is directed to a dental extruder or syringe for manually extruding dental material from a cartridge having a body and wider flange portion. The front end of the extruder or syringe has a front end with rigid side walls and a longitudinal slot or opening therein. The lateral width of the opening or slot is larger than the diameter of the body portion of a cartridge. Adjacent the longitudinal slot or cartridge body opening is a cartridge flange retainer. The cartridge flange retainer has a circumference at least as great as the diameter of the flange on a cartridge. Adjacent the flange retainer is a lateral slot or flange opening. The flange opening has a lateral width wider than the diameter of the flange of the cartridge, and a longitudinal length greater than the axial length of the flange. A shoulder or inturned flange is formed between the flange retainer and the longitudinal slot or cartridge body opening which acts as a bearing surface for the front surface of the flange of the cartridge. The front portion of the barrel is made from a rigid material which prevents the flexing of the side walls and therefore separation of the cartridge from the syringe during high extrusion pressures. Because the cartridge has a body portion with a diameter less than the lateral width of the cartridge body opening and the flange of the cartridge has a diameter less than the lateral width of the flange opening, the cartridge is easily dropped into the front end portion of the dental extruder or syringe. Once positioned in the front end portion, the cartridge is slid forward or pushed forward by an advancing plunger and thereby retained in the front end portion by the flange retainer. The plunger is advanced forward by a handle with a cam surface. The plunger is biased with a spring so the front end of the plunger is normally retracted beyond the flange opening. The cartridge is removed by pushing back the cartridge so that the flange of the cartridge is within the flange opening and outside of the flange retainer. The cartridge is then easily removed.

It is an object of the present invention to provide a dental extruder or syringe that is easy to load and use.

It is another object of the present invention to provide a dental extruder or syringe that will securely retain a cartridge filled with viscous dental material.

It is an advantage of the present invention that it has increased strength and a reduced likelihood of breakage due to fatigue.

It is another advantage of the present invention that exterior stresses on the side walls of a cartridge is eliminated during insertion and removal of the cartridge.

It is a feature of the present invention that the front end portion has rigid side walls.

It is another feature of the dental extruder or syringe of the present invention that the longitudinal slot or front end opening has a lateral width equal to or larger than the diameter of the body portion of a cartridge.

It is a further feature of the present invention that a flange retainer is used to securely hold the flange during extrusion of a dental cartridge.

It is yet another feature of the present invention that a plunger and cam surface on a handle are adapted so that a spring biases the front of the plunger beyond the flange opening the barrel facilitating insertion and removal of a dental cartridge.

These and other objects, advantages, and features will become readily apparent in view of the following more detailed description and figures.

DETAILED DESCRIPTION OF THE PREFERRED EMBODIMENTS

Figure 1:
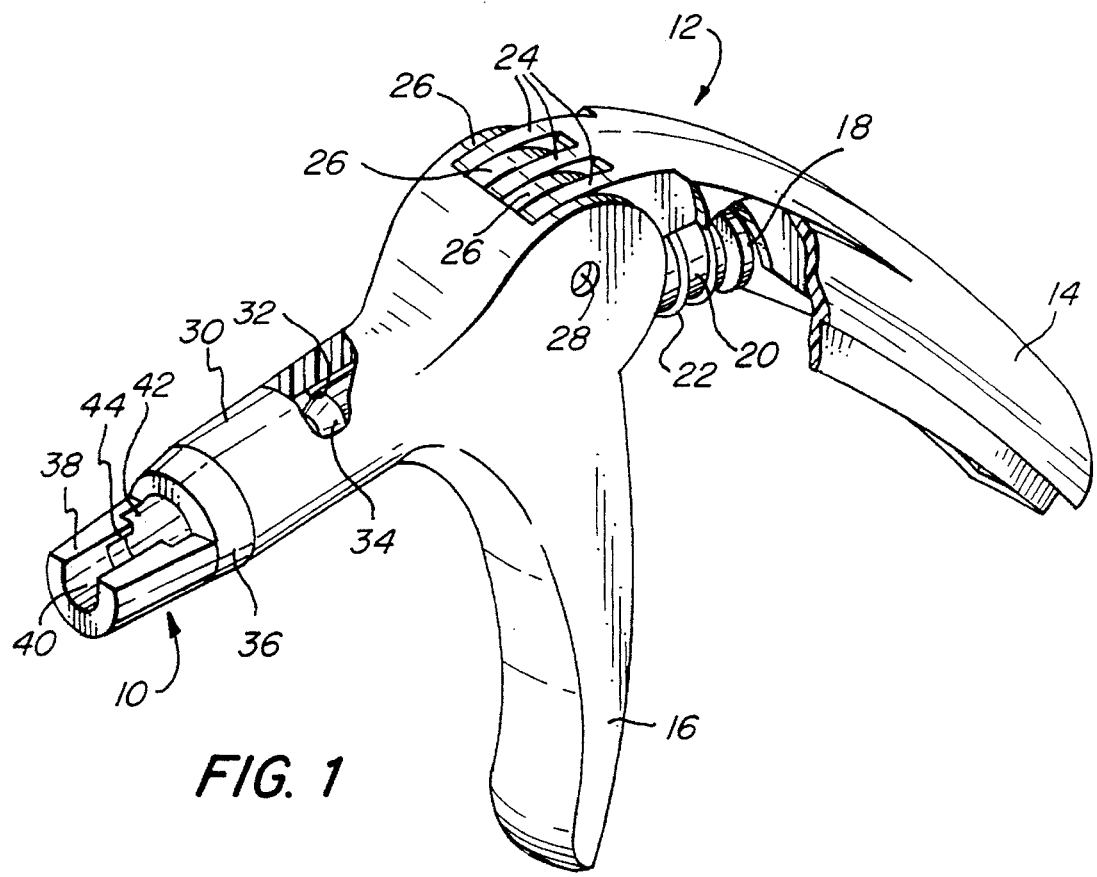
FIG. 1 is a perspective view with partial sectioning illustrating the present invention.

FIG. 1 illustrates the dental extruder or syringe of the present invention. Generally, the extruder has a front end 10 and a handle portion 12. The handle portion 12 comprises a rear handle 14 attached to a front handle 16. The rear handle 14 has a cam surface 18 thereon. The cam surface 18 advances a plunger 20 through a barrel bore 32 in a barrel 30 attached to the front handle 16. The plunger 20 is biased outward by spring 22. The rear handle 14 and the front handle 16 are attached by rear handle hinge fingers 24 and front handle hinge fingers 26. The rear handle 14 and front handle 16 are held in place by a pivot pin 28. The handle portion of the present invention has a construction similar to that of the dental syringe disclosed in U.S. Pat. No. 4,198,756 or U.S. Pat. No. 5,061,179, which is herein incorporated by reference.

The front end 10 of barrel 30 has a reduced portion 36 and rigid side walls extending to the distal end of the barrel 30 terminating in a front opening. The rigid side walls 38 are constructed of a material so that they are strong, durable, and will not flex substantially. Many plastics have these characteristics. A fully aromatic polyester plastic such as Vectra liquid crystal polymer has these characteristics. The rigid side walls 38 form a cartridge body opening 40 and a cartridge chamber. The cartridge body opening 40 is adapted to receive a dental cartridge or ampule having a substantially cylindrical body portion with a larger diameter flange on one end and a nozzle at the other end. One such cartridge, capsule, ampule, or tip for containing a single or unit dose of dental filling material is disclosed in U.S. Pat. No. 4,963,093, which is herein incorporated by reference. Adjacent the cartridge body lateral opening 40 is a flange chamber having a flange opening 42. The flange opening 42 has a lateral width or diameter greater than the lateral width of the cartridge body opening 40. Between the cartridge body opening 40 and the flange opening 42 is a flange retainer or recess 44 having a lateral opening substantially equal to the width of opening 40. The cartridge body opening 40 has a lateral width that is equal to or greater than the outside diameter of a cartridge or ampule body containing dental material. The lateral width of the flange opening 42 is larger than the outside diameter of the flange 52 of a cartridge. The flange retainer portion or recess 44 has an inner circumference adapted to receive or generally matching that of the outside flange diameter of a cartridge.

In operation, the body portion of a dental cartridge or ampule is dropped into the front end portion 10, laterally whereby the body portion of the cartridge or ampule easily passes through the larger lateral cartridge body opening 40 with the larger diameter flange easily passing or dropping through the larger flange lateral opening 42. The cartridge is then advanced or shifted forward away from the handle and toward the front end of the barrel so that the flange of the cartridge enters the recess 44 and is retained by the recess or flange retainer 44. The cartridge may be positioned by hand to seat the flange 52 within the recess or flange retainer or advanced forwardly by the plunger front end 34 as the rear handle 14 is squeezed towards front handle 16 causing the plunger 20 to seat the flange 52 in the recess or the retainer 44. The plunger 20 and cam surface 18 are configured or adapted so that when the handle is pushed back by the spring 22 and plunger 20, the plunger 20 always maintains contact with the cam surface 18. In this position the front end of the plunger 20 is adjacent the flange opening 42. This permits easy removal of the cartridge without having to remove the plunger 20 from contact with the cam surface 18 and the handle 14.

Figure 2:
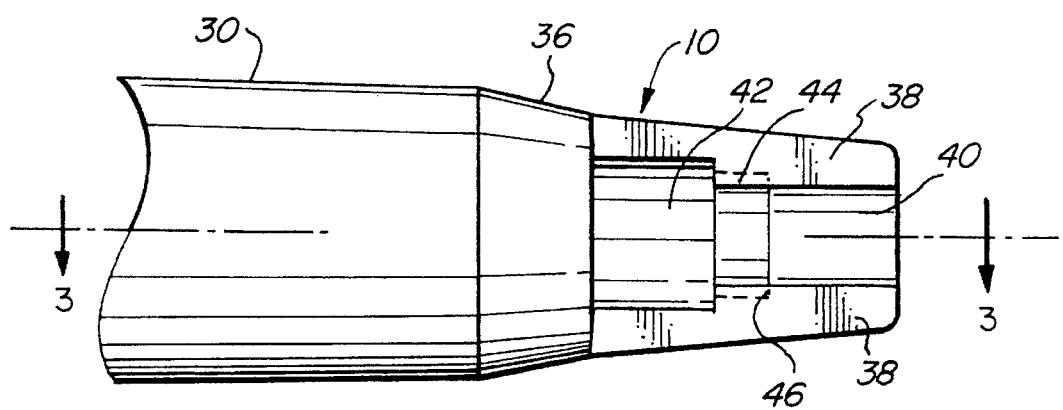
FIG. 2 is a top plan view of a portion of the front end of the present invention.
Figure 3:
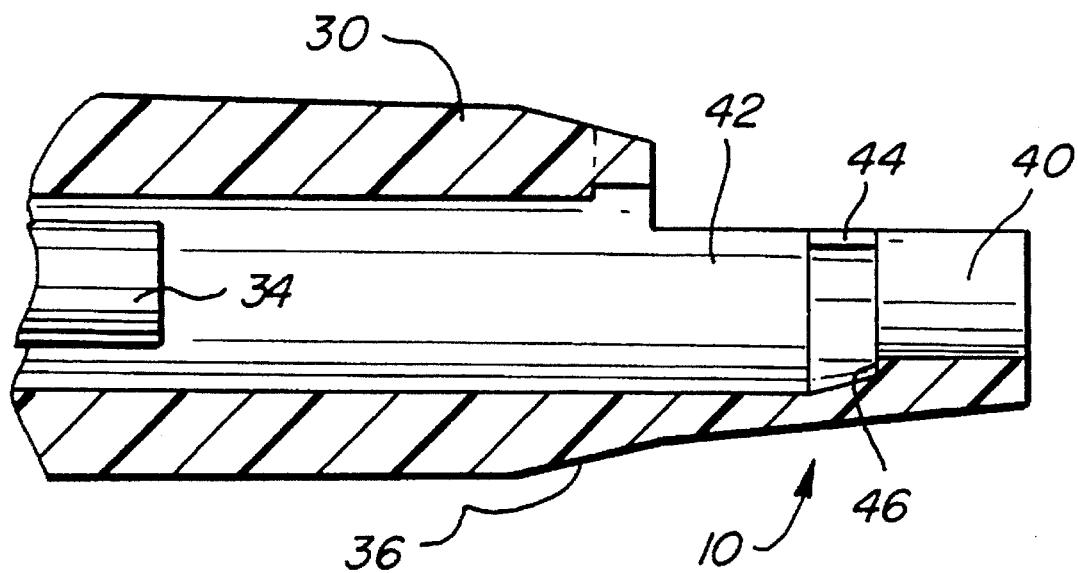
FIG. 3 is a cross section taken along line 3—3 in FIG. 2.
Figure 4:
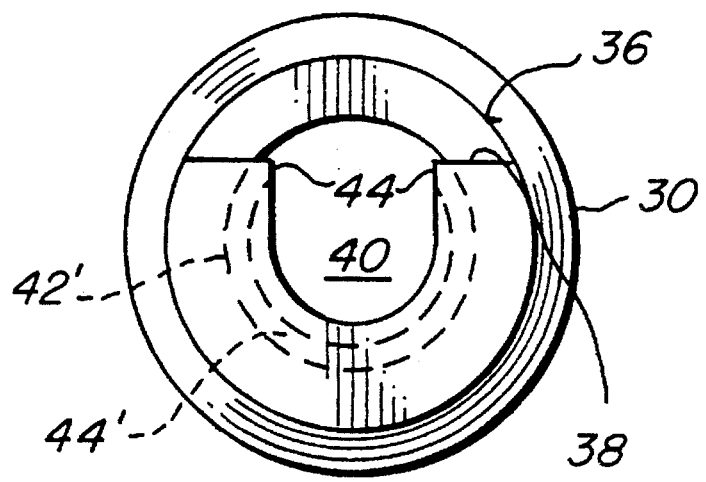
FIG. 4 is an elevational view illustrating the front end portion of the present invention.

FIGS. 2, 3, and 4 more clearly illustrate the front end portion of the dental extruder or syringe gun of the present invention. As can more clearly be seen in FIG. 2, the lateral width of cartridge body opening 40 is substantially constant along its length. This lateral width is always equal to or slightly greater than the outside diameter of the body portion of a cartridge intended to be inserted into the dental extruder or syringe gun device of the present invention. The rigid side walls 38, being extremely rigid, will not permit the insertion of a cartridge having a body portion with an outside diameter greater than that of the lateral width of cartridge body opening 40. Adjacent to the rear of the cartridge body opening 40 is the flange opening 42. The flange opening 42 has a lateral width greater than the lateral width of cartridge body opening 40. The lateral width of the flange opening 42 is always greater than the outside diameter of the flange portion 52 of a cartridge. Between the cartridge body opening 40 and the flange opening 42 is a recess or flange retainer 44. The flange retainer 44 is recessed into a rear portion of the cartridge body opening 40. The recess or flange retainer 44 has an inner circumferential surface that is substantially the same as the outer diameter of the flange of the dental cartridge so as to receive the flange 52. The lateral width of the opening over the flange retainer 44 is the same as that of the cartridge body opening 40 and less than the diameter of the cartridge flange. An upper retaining surface is thereby formed as well as a flange bearing shoulder 46 at the forward end of the flange retainer 44.

FIG. 3 is a cross section taken along line 3—3 in FIG. 2. In FIG. 3 the shoulder 46, which will provide most of the support for the longitudinal forces on the cartridge during extrusion, can more clearly be seen.

FIG. 4 is a front elevational view of the front end portion 10 illustrating the various concentric circumferences formed therein. Circumferential surface 42' is that of the flange opening circumference. Circumferential surface 44' is that of the recess or flange retainer 44.

Figure 5A:
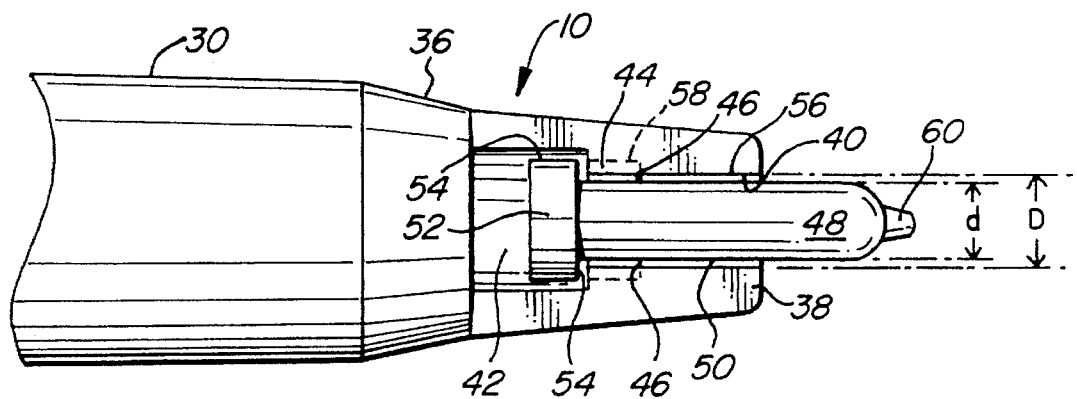
FIG. 5A is a top plan view of a portion of the front end of the present invention illustrating the initial placement of a cartridge.
Figure 5B:
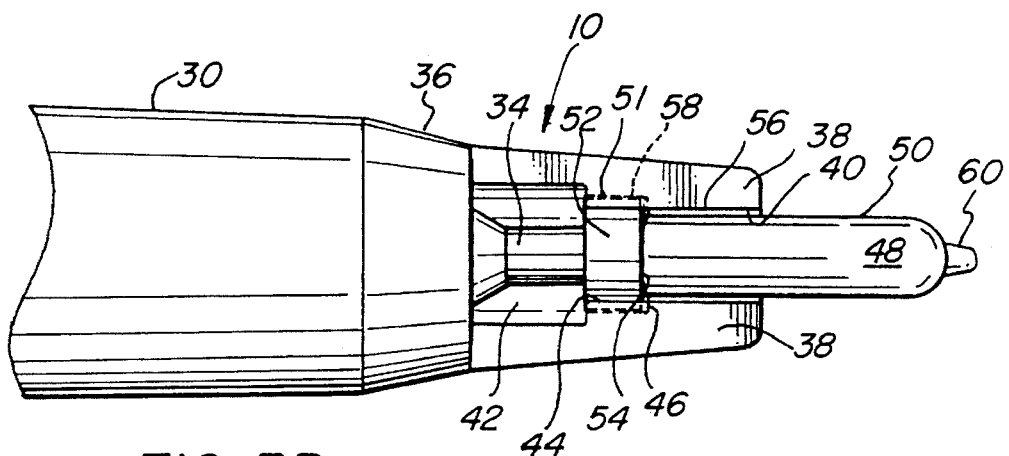
FIG. 5B is a top plan view of the present invention illustrating the positioning of a cartridge for extruding.

FIGS. 5A and 5B illustrate the front end portion of the present invention and its use with a cartridge 48. Cartridge 48 contains dental material to be extruded. The dental material in cartridge 48 is generally very viscous requiring high extrusion pressures, resulting in large longitudinal forces being placed on the cartridge during extrusion. The cartridge 48 is of generally cylindrical shape and has an outer body surface 50. The lateral width or diameter of the outer body surface 50 of the body of the cartridge 48 is represented by d. (FIG. 5) The rear portion of the cartridge 48 has a flange 52. The flange 52 has an outer circumferential surface 51. The lateral width or diameter of the flange 52 is less than that of the lateral width of flange opening 42. The flange 52 has a front bearing surface 54. The front bearing surface 54 is adapted to mate with the shoulder 46. The inner surface 56 of cartridge opening 40 has a lateral width represented by D. The lateral width D is always greater than the lateral width d. This permits easy loading of the cartridge 48 into the front portion 10 of the dental extruder or syringe gun. The recess flange retainer 44 has an inner circumferential surface 58. FIG. 5B illustrates the final positioning of the cartridge 48. Cartridge 48 is moved or shifted forward after being placed within the front end portion 10. A portion of the recess or flange retainer 44 encircles or covers a portion of the flange 52 of cartridge 48. This prevents the cartridge 48 from being moved upwards out of the cartridge body opening 40. The flange retainer 44 additionally holds the flange front bearing surface 54 in contact with shoulder 46. Shoulder 46 prevents further forward movement of the cartridge 48 during extrusion. The forward motion of the cartridge 48 into the recess or flange retainer 44 may be accomplished by manually pulling the end of the cartridge 48 forward, or by the advancing plunger just prior or during the extrusion operation. After the cartridge 48 is securely seated against shoulder 46, the extrusion begins forcing viscous dental material through nozzle 60. Once extrusion begins, the cartridge 48 is securely held in the front end 10 by the action of the plunger. After extrusion, the plunger is pushed back by the spring 22 permitting the cartridge 48 to be slid rearward releasing it from the flange retainer 44. The cartridge is then easily lifted out of the front end portion 10. As there is no "snap-fit" or friction fit between the rigid side walls 38 and the outer surface 50 of the cartridge body, the cartridge 48 can easily be removed.

Figure 6:
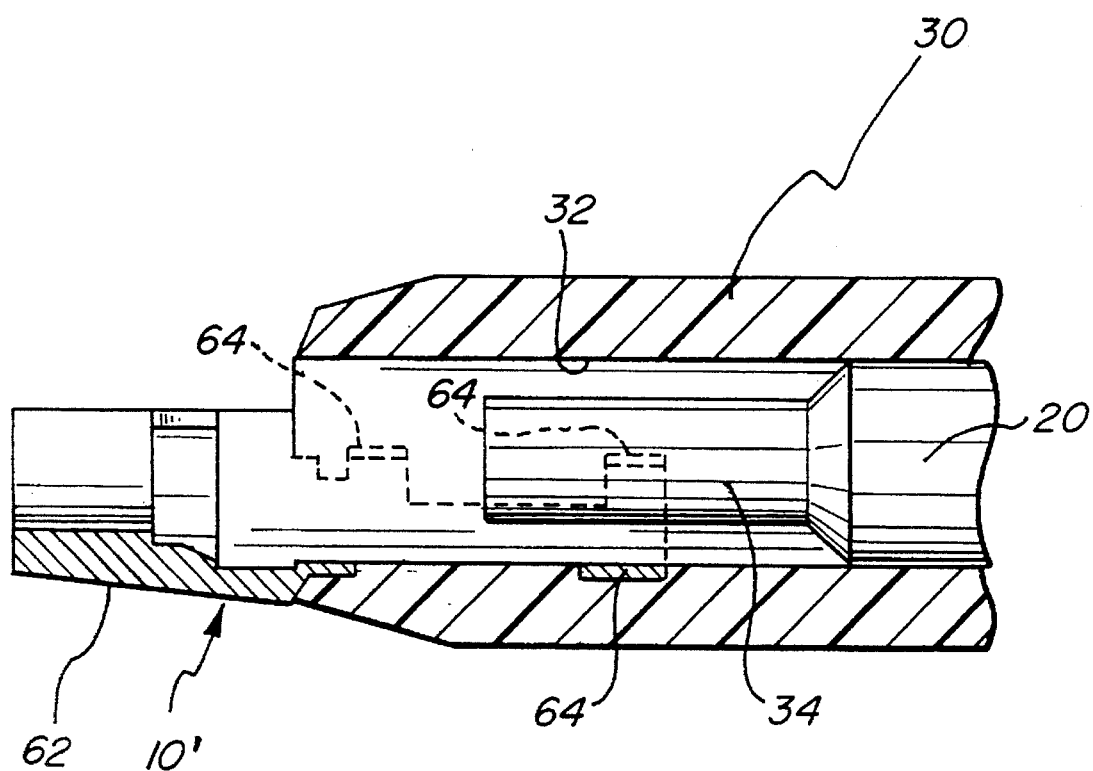
FIG. 6 is a cross section of a second embodiment of the present invention illustrating a metal insert front end portion.

FIG. 6 illustrates a second embodiment of the present invention. In this embodiment, a metal insert 62 is inserted into a plastic barrel 30. The metal insert is held securely within the plastic barrel 30 by shaped retainers 64 of the metal insert 62. The metal insert has the same general configuration as previously described for the prior embodiment. The use of a metal insert in the present invention is molded to the front end of the plastic barrel in a manner described in U.S. patent application Ser. No. 08/082,464 filed Jun. 28, 1993, which is herein incorporated by reference, and is now U.S. Pat. No. 5,306,147.

It should now be appreciated, in view of the foregoing description, that the present invention provides an ease of insertion and secure holding of a dental cartridge that has not previously been possible with prior dental extruders or syringes. Additionally, hoop stresses on the dental cartridge are reduced because there are no stresses on the body portion of the cartridge due to a "snap-fit". Additionally, the lateral forces on the front end that often cause fatigue and failure are eliminated.

Although the preferred embodiments have been illustrated and described, it will be obvious to those skilled in the art that various modifications and variations may be made without departing from the spirit and scope of this invention.

What is claimed is:

1. A dental extruder comprising:

a handle portion;

a barrel attached to said handle portion, said barrel having a distal front end portion terminating in a front opening and a side wall defining a cartridge chamber;

a plunger slidably positioned within said barrel;

said distal front end portion having a longitudinally extending cartridge body opening formed in said side wall extending to said front opening, said cartridge body side opening having a lateral width greater than the diameter of a cartridge body to provide a means for unobstructed insertion and removal of a cartridge body adapted to be received therein, said distal front end portion being made of a substantially inflexible, rigid material;

said distal front end portion including a flange side opening adjacent said cartridge body side opening and rearwardly thereof, said flange side opening having a lateral width at least as great as the diameter of a flange on a cartridge adapted to be received therein; and retaining means between said cartridge body side opening and said side flange opening for receiving and positively retaining a cartridge flange adapted to be received within said retaining means, said retaining means being adapted to circumscribe a major portion of the diameter of the flange of a cartridge.

2. A dental extruder as in claim 1 wherein:

said retaining means comprises a recess in said distal front end portion substantially centered on the longitudinal axis of said barrel and having a circumference adapted to circumscribe a major portion of a flange of a cartridge adapted to be received therein.

3. A dental extruder as in claim 1 wherein:

said handle portion has a distal downwardly extending portion; and said cartridge body side opening is placed in the top of said distal front end portion opposite the distal downwardly extending portion of said handle portion, whereby said cartridge can be easily inserted into the cartridge body opening and held in position by gravity prior to being advanced forward by said plunger and positively secured into position for extrusion of dental material.

4. A dental extruder comprising:

a handle portion;

a barrel attached to said handle portion, said barrel having a distal front end portion having a side wall and terminating in a front opening;

a plunger slidably positioned within said barrel;

said distal front end portion having a longitudinal cartridge body side opening formed in said side wall and extending to said front opening, said cartridge body side opening having a lateral width greater than the diameter of a cartridge adapted to be received therein, said distal front end portion being made of a rigid material;

said distal front end portion including a flange side opening therein adjacent said cartridge body side opening, said flange side opening having a lateral width greater than the diameter of a flange on the cartridge adapted to be received therein; and retaining means, between said cartridge side body opening and said flange side opening, for retaining the flange therein;

said retaining means being a recess formed in said distal front end portion substantially centered on the longitudinal axis of said barrel forwardly of said flange side opening and having a circumference adapted to receive the flange of the cartridge;

said barrel being made of plastic and said distal front end portion being a metal insert secured to said plastic barrel.

5. A dental extruder comprising:

a handle portion;

a cylindrical barrel having a distal front end portion attached to said handle portion;

a plunger slidably positioned within said barrel;

said distal front end portion having inflexible, rigid side walls, a cartridge body side opening and a connected flange side opening formed in a lateral surface of said side walls, each of said side openings having a longitudinal axis substantially parallel to the longitudinal axis of said barrel;

a dental cartridge having a flange at one end and a nozzle at the other end with a body portion in between, said body portion having a first diameter and said flange having a second larger diameter;

said cartridge body side opening having a lateral width greater than the first diameter of the body portion of said dental cartridge to provide a means for unobstructed insertion and removal of said cartridge body portion adapted to be received therein;

said flange side opening having a lateral width greater than the second diameter of the flange of said dental cartridge; and a flange retainer formed within said side wall and positioned in axial alignment with said cartridge body side opening and said flange side opening and having an internal circumference sized to receive the flange of said cartridge, whereby a portion of the inflexible, rigid side walls defining said cartridge body side opening extends over the flange of said dental cartridge when said dental cartridge is seated in said flange retainer in a position to be extruded.

6. A dental extruder comprising:

a barrel, said barrel having a distal front end portion;

a front handle attached to said barrel;

a rear handle, said rear handle pivotally attached to said front handle;

a cam surface on said rear handle;

a plunger slidably positioned within said barrel, said plunger having a front and rear end;

a spring surrounding said plunger, said spring biasing said plunger away from said front handle such that the rear end of said plunger contacts said cam surface; and a dental cartridge having a tubular body portion and a flange on one end;

the front end portion of said barrel having a longitudinal cartridge body opening therein extending to the distal end, the cartridge body opening having a lateral width at least as great as the diameter of the tubular body portion of said dental cartridge, said front end portion being made of a rigid material;

the front end portion of said barrel having a flange opening therein adjacent the cartridge body opening, said flange opening having a lateral width at least as great as the diameter of the flange on one end to said cartridge;

said front end portion of said barrel having a recess between said cartridge body opening and said flange opening, said recess being substantially centered on the longitudinal axis of said barrel and having a circumference adapted to receive the flange on one end of said cartridge;

whereby said dental cartridge is dropped into the front end by the body portion passing through the cartridge body opening and the flange passing through the flange opening, said dental cartridge sliding forward and locking into position when the recess receives the flange and said plunger is advanced forward.

7. A dental extruder adapted for extruding the contents of a dental cartridge having a cylindrical body portion and a circumscribing laterally extending flange comprising:

a handle portion, a barrel formed of a rigid material attached to said handle portion, said barrel having a distal front end portion terminating in a front opening, said distal front end portion defining a cartridge chamber having a side opening formed in said distal front end portion and extending to said front opening, said cartridge chamber side opening having a width slightly greater than the diameter of the body portion of a cartridge adapted to be received in said cartridge chamber, said distal front end portion including a flange side opening having a lateral width slightly greater than the diameter of the cartridge flange, retaining means disposed between said cartridge chamber side opening and said flange side opening, said retaining means including a recess formed forwardly of said flange side opening and rearwardly of said cartridge chamber side opening, said recess having a diameter sized to receive the flange of the cartridge adapted to be seated in said cartridge chamber, and said recess having a side opening having a lateral width at least as wide as said cartridge chamber side opening and less than the diameter of the cartridge flange, and a plunger slidably positioned within said barrel for effecting the extrusion of the cartridge contents.

8. A dental extruder as in claim 7 wherein:

said barrel and said distal front end portion are made of a non flexing plastic.

9. A dental extruder as in claim 7 further comprising:

spring means, associated with said plunger for biasing said plunger away from said barrel distal front end portion.

10. A dental extruder as in claim 7 wherein said handle portion comprises:

a rear handle;

a front handle attached to said barrel, said rear handle pivotally attached to said front handle; and a cam surface on said rear handle;

whereby when said rear handle is moved an end of said plunger contacts said cam surface.

11. A dental extruder as in claim 10 wherein:

said plunger and said cam surface are adapted so that the front end of said plunger is adjacent the flange opening when said spring means biases said plunger away from said barrel front end portion and the rear end of said plunger is contacting said cam surface.

12. A dental extruder as defined in claim 7 wherein said cartridge chamber side opening of said cartridge chamber, said flange side opening and said lateral opening of said retaining recess therebetween are co-axially disposed parallel to the longitudinal center of said barrel.

13. A dental extruder comprising:

a handle portion;

a cylindrical barrel attached to said handle portion;

a plunger slidably positioned within said barrel;

said barrel including a front end, said front end having rigid side walls forming a cartridge body chamber having a side body opening and a flange chamber having a side flange opening, each of the body and flange side openings being formed in the longitudinal side surface of the front end of said barrel, and having a longitudinal axis substantially parallel to the longitudinal axis of said barrel;

a dental cartridge having a flange at one end and a nozzle at the other end with a body portion in between, the body portion having a first diameter and the flange having a second larger diameter;

the side body opening having a lateral width at least as wide as the first diameter of the body portion of said dental cartridge;

the side flange opening having a lateral width wider than the second diameter of the flange of said dental cartridge; and a flange retainer recess positioned between the cartridge body chamber and the flange chamber formed within the rigid side walls, said flange retainer recess having a circumference adapted to receive the flange of said dental cartridge, whereby a circumferential portion of the rigid side walls defining said recess extends over a circumferential portion of more than 180 degrees of the flange of said dental cartridge when said dental cartridge is in a position to be extruded.

14. A dental extruder comprising:

a barrel, said barrel having a distal front end portion terminating in a front opening;

a front handle attached to said barrel;

a rear handle, said rear handle pivotally attached to said front handle;

a cam surface on said rear handle;

a plunger slidably positioned within said barrel, said plunger having a front and rear end;

a spring surrounding said plunger, said spring biasing said plunger away from said front handle such that the rear end of said plunger contacts said cam surface; and a dental cartridge having a tubular body portion and a flange on one end;

the distal front end portion of said barrel defining a cartridge chamber having a lateral cartridge body opening extending longitudinally and formed in a longitudinal side surface of the distal front end portion of said barrel and extending to the front opening, the cartridge body opening having a lateral width at least as great as the diameter of the tubular body portion of said dental cartridge to provide a means for unobstructed insertion and removal of said cartridge body portion adapted to be received therein, the distal front end portion being made of a rigid material;

a lateral flange opening extending longitudinally and formed in a longitudinal side surface of the distal front end portion of said barrel and disposed adjacent the lateral cartridge body opening, the lateral flange opening having a lateral width for receiving the diameter of the flange on one end of said dental cartridge;

the distal front end portion of said barrel including a flange recess disposed rearwardly of said cartridge chamber and forwardly of said flange opening, said recess being substantially centered on the longitudinal axis of said barrel and having a circumference adapted to receive the flange of said cartridge;

whereby said dental cartridge can be readily positioned into the distal front end portion so that the cartridge body portion freely passes through the cartridge body opening and the flange freely passes through the flange opening, and said dental cartridge being locked into position by a forward shifting of said dental cartridge for seating the flange in the recess.

15. A dental extruder comprising:

a barrel having a distal front end portion terminating in a front opening;

said distal front end portion defining a cartridge chamber for receiving a dental cartridge having a cartridge body and a connected flange;

said distal front end portion having a longitudinal extending cartridge body side opening extending to said front opening, said cartridge body side opening having a lateral width greater than the diameter of a body of a cartridge to provide the means to allow a cartridge body to be unobstructedly inserted and removed through said cartridge body side opening to seat a cartridge in said cartridge chamber, said distal front end portion being made of a substantially inflexible, rigid material; and said distal front end portion including a flange side opening formed rearwardly of said cartridge body side opening, said flange side opening having a lateral width slightly greater than the diameter of the flange of a cartridge; and retaining means disposed rearwardly of said cartridge chamber and forwardly of said flange side opening, for positively retaining the flange therein;

and a plunger slidably positioned within said barrel whereby the actuation of said plunger seats the cartridge flange in said retaining means.

16. A dental extruder comprising:

a handle portion;

a barrel attached to said handle portion, said barrel having a distal front end portion terminating in a front opening;

a plunger slidably positioned within said barrel;

a cartridge having a cylindrical body and a connected flange;

said distal front end portion defining a cartridge chamber having a longitudinal cartridge body opening formed in a side wall of said distal front end portion and extending to said front opening;

said cartridge body opening having a lateral width slightly greater than the diameter of said cylindrical body of said cartridge, said distal front end portion being made of a rigid material;

a flange side opening formed in the side wall of said distal front end portion adjacent the cartridge body opening and to the rear thereof, said flange side opening having a lateral width slightly greater than the diameter of said flange on said cartridge; and retaining means disposed between said cartridge chamber and said flange side opening for receiving and retaining said cartridge flange therein;

said retaining means comprising a recess formed to the rear of said cartridge chamber substantially centered on the longitudinal axis of said barrel and having a circumference sized to receive said flange of said cartridge;

said barrel being formed of plastic and said distal front end portion comprising a metal insert connected to said plastic barrel.

17. A dental extruder adapted for extruding the contents of a dental cartridge having a cylindrical body portion and a circumscribing laterally extending flange comprising:

a handle portion, a barrel formed of a rigid material attached to said handle portion, said barrel having a distal front end portion terminating in a front opening, said distal front end portion defining a cartridge chamber having a cartridge lateral side opening extending to said front opening, said cartridge chamber lateral side opening having a width slightly greater than the diameter of a body portion of a cartridge adapted to be received in said chamber, said distal front end portion including a cartridge flange receiving chamber, said cartridge flange receiving chamber having a lateral flange side opening having a width slightly greater than the diameter of a cartridge flange, a retaining means disposed between said cartridge chamber and said lateral flange receiving chamber, said retaining means comprising a recess disposed rearwardly of said cartridge chamber and forwardly of said flange receiving chamber, said recess having a diameter sized to receive the flange of a cartridge adapted to be seated in said cartridge chamber, and said recess having a side opening at least as wide as said cartridge chamber side opening and smaller than the diameter of a cartridge flange, and a plunger slidably positioned within said barrel for effecting the extrusion of a cartridge contents.

18. A manual extruder comprising:

an elongated barrel having a distal front end portion formed of a rigid, non-flexible material terminating in a front opening;

said distal front end portion having a longitudinal side wall portion;

a cartridge body opening formed in said longitudinal side wall portion of said distal front end portion, and said cartridge body opening extending to said front opening to define a cartridge chamber adapted to receive a cartridge having a cylindrical body portion and a connected flange;

said cartridge body opening having width greater than the diameter of the body portion of a cartridge to provide a means for the unobstructed insertion and removal of a cartridge adapted to be inserted into said cartridge chamber;

a flange opening formed in said longitudinal side wall portion rearwardly of said cartridge body opening and connecting with said cartridge body opening;

said flange opening having a lateral width slightly greater than the diameter of a cartridge flange for allowing the flange of a cartridge to be inserted therethrough as the cartridge body is inserted through said cartridge body opening;

and a recess formed in said longitudinal side wall portion internally thereof, rearwardly of said cartridge chamber and forwardly of said flange opening;

said recess having a diameter sized to receive the flange of a cartridge for positively securing the cartridge within the distal front end portion;

and a piston slidably mounted in said elongated barrel.

* * * * *